(12) United States Patent
Kondo

(10) Patent No.: US 10,175,678 B2
(45) Date of Patent: Jan. 8, 2019

(54) AUTOMATIC THIN-CUTTING DEVICE, PARAMETER GENERATION DEVICE, AUTOMATIC THIN-CUTTING METHOD, AND PROGRAM

(71) Applicant: SAKURA FINETEK JAPAN CO., LTD., Tokyo (JP)

(72) Inventor: Megumi Kondo, Tokyo (JP)

(73) Assignee: SAKURA FINETEK JAPAN CO., LTD., Tokyo (JP)

( * ) Notice: Subject to any disclaimer, the term of this patent is extended or adjusted under 35 U.S.C. 154(b) by 411 days.

(21) Appl. No.: 14/650,450

(22) PCT Filed: Nov. 21, 2013

(86) PCT No.: PCT/JP2013/081412
§ 371 (c)(1),
(2) Date: Jun. 8, 2015

(87) PCT Pub. No.: WO2014/091898
PCT Pub. Date: Jun. 19, 2014

(65) Prior Publication Data
US 2015/0323925 A1    Nov. 12, 2015

(30) Foreign Application Priority Data

Dec. 11, 2012  (JP) ................................ 2012-270169

(51) Int. Cl.
*G01N 1/06*     (2006.01)
*G01N 1/30*     (2006.01)
(Continued)

(52) U.S. Cl.
CPC .......... *G05B 19/4086* (2013.01); *G01N 1/06* (2013.01); *G01N 35/00732* (2013.01);
(Continued)

(58) Field of Classification Search
None
See application file for complete search history.

(56) References Cited

U.S. PATENT DOCUMENTS 7,374,907 B1   5/2008 Voneiff et al.
2003/0022271 A1  1/2003 Voneiff et al.
(Continued)

FOREIGN PATENT DOCUMENTS

CN   102297873   12/2011
JP   2004-028910   1/2004
(Continued)

OTHER PUBLICATIONS

Roy Ellis, "Problems in Histopathological Technique", 2002, IHCWORLD, pp. 1-4 (Year: 2002).*
(Continued)

*Primary Examiner* — Kathryn Wright
(74) *Attorney, Agent, or Firm* — Grossman, Tucker, Perreault & Pfleger, PLLC

(57) ABSTRACT

An acquisition part (10, 11, 12) acquires a plurality of types of data of tissue used to form a pathological section specimen. A storage part (13) stores the data of the tissue. A parameter generation part (14) generates parameters, which are used when preparing the pathological section specimen, based on the data of the tissue acquired by the acquisition part (10, 11, 12). A pathological section specimen preparation part (15) prepares the pathological section specimen using the parameters generated by the parameter generation part (14).

6 Claims, 2 Drawing Sheets

(51) Int. Cl.
*G05B 19/408* (2006.01)
*G05B 15/02* (2006.01)
*G01N 35/00* (2006.01)
*G01N 1/31* (2006.01)

(52) U.S. Cl.
CPC ............... *G05B 15/02* (2013.01); *G01N 1/31* (2013.01); *G01N 1/312* (2013.01); *G05B 2219/37087* (2013.01)

(56) References Cited

U.S. PATENT DOCUMENTS

| | | | |
|---|---|---|---|
| 2005/0095666 A1 | 5/2005 | Jhavar et al. | |
| 2005/0235542 A1 | 10/2005 | Metzner et al. | |
| 2007/0141711 A1 | 6/2007 | Stephens et al. | |
| 2008/0235055 A1 | 9/2008 | Mattingly et al. | |
| 2010/0030364 A1 | 2/2010 | Fujimoto et al. | |
| 2010/0050839 A1* | 3/2010 | Miyatani | G01N 1/06 83/155.1 |
| 2010/0101385 A1 | 4/2010 | Walter et al. | |
| 2010/0229702 A1 | 9/2010 | Fujimoto et al. | |
| 2014/0086463 A1* | 3/2014 | Meetz | G01N 1/06 382/128 |

FOREIGN PATENT DOCUMENTS

| | | | |
|---|---|---|---|
| JP | 2007-212386 | 8/2007 | |
| JP | 2007-212388 | 8/2007 | |
| JP | 4548356 | 7/2010 | |
| JP | 4548357 | 7/2010 | |
| JP | 2010-261762 | 11/2010 | |
| JP | 2010-261763 | 11/2010 | |
| WO | WO 2012156862 A1 * | 11/2012 | ............... G01N 1/06 |

OTHER PUBLICATIONS

Office Action from related Chinese Application No. 201380063985.6 dated May 5, 2016. English translation attached.

Search Report from related EPO Application No. 13863286.4 dated Jul. 6, 2016.

International Search Report from corresponding PCT Application No. PCT/JP2013/081412 dated Dec. 24, 2013. English translation attached.

Notice of Allowance from related Japanese Application No. 12012-270169 dated Jun. 6, 2017. English translation attached.

\* cited by examiner

| ORGAN TYPE | DYEING METHOD | DEFATTING STATE | DECALCIFICATION STATE | ROUGH CUTTING RECIPE | MAIN CUTTING RECIPE | SPREADING RECIPE | USED SLIDE GLASS | USED DYEING CASE | |
|---|---|---|---|---|---|---|---|---|---|
| T1 | S1 | Y | N | F1 | Sc1 | F1 | 1 | 1 | ROW 201 |
| T1 | S1 | N | Y | F1 | Sc2 | F2 | 1 | 1 | ROW 202 |
| T1 | S2 | Y | N | F2 | Sc3 | F3 | 2 | 3 | ROW 203 |
| T2 | S1 | Y | N | F4 | Sc1 | F5 | 1 | 1 | ROW 204 |

AUTOMATIC THIN-CUTTING DEVICE, PARAMETER GENERATION DEVICE, AUTOMATIC THIN-CUTTING METHOD, AND PROGRAM

TECHNICAL FIELD

The present invention relates to an automatic thin-cutting device, a parameter generation device, an automatic thin-cutting method, and a program.

Priority is claimed on Japanese Patent Application No. 2012-270169, filed on Dec. 11, 2012, the content of which is incorporated herein by reference.

BACKGROUND ART

The automation of a section preparation process, in the process of preparing a pathological section specimen, has been delayed due to the complexity of the work. The section preparation process is a step of pasting a section, which is obtained by thin-cutting a paraffin block in which tissue is embedded, on a slide glass. In recent years, however, devices for automating the section preparation process have been developed (for example, refer to Patent Documents 1 to 3).

However, in the device disclosed in Patent Document 1, only the setting of a block, thin-cutting, section collecting, and pasting to the glass are automated. For this reason, the user needs to directly set the preparation conditions, such as the thickness of a section or the cutting speed, for each block.

In the device disclosed in Patent Document 2, a preparation condition table is provided. Accordingly, it is possible to set the preparation conditions by referring to the preparation condition table based on the storage location of the block. In the device disclosed in Patent Document 3, a preparation condition table is provided. Accordingly, it is possible to set the preparation conditions by referring to the preparation condition table based on the ID of a cassette.

PRIOR ART DOCUMENTS

Patent Documents

Patent Document 1: Japanese Unexamined Patent Application, First Publication No. 2004-28910
Patent Document 2: Japanese Patent No. 4548356
Patent Document 3: Japanese Patent No. 4548357

SUMMARY OF INVENTION

Problems to be Solved by the Invention

However, in the devices disclosed in Patent Documents 2 and 3, normally the user does not quantitatively know the parameters of the preparation conditions which are set for each block storage location or each cassette ID. Accordingly, it has been difficult to deal with such parameters.

On the other hand, in a hospital where pathological section specimens are mainly prepared, introduction of an online system is in progress in order to prevent diagnostic errors due to confusion of the specimens. Accordingly, there is a high demand for the online automatic section preparation device. However, since the online system that has already been introduced has not been designed in consideration of the online automatic section preparation device, data required for section preparation is not included in the online system. In addition, it is difficult to upgrade the online system that has already been introduced in terms of cost or time and effort. These have been factors that inhibit the building of the online automatic section preparation device.

Even in the online automatic section preparation device, there is a case in which a user directly inputs the section preparation conditions temporarily. However, since the section preparation so far has been performed based on the sense of the user, it is difficult for the user to deal with and understand the numerical section preparation conditions. As a result, there has been a problem that it is difficult to use the automatic section preparation device.

Aspects of the present invention have been made in view of the aforementioned situation, and it is an object of the present invention to provide an automatic thin-cutting device, a parameter generation device, an automatic thin-cutting method, and a program that can automatically more flexibly generate parameters which are used when preparing a pathological section specimen.

Means for Solving the Problems

An automatic thin-cutting device according to an aspect of the present invention includes: an acquisition part configured to acquire a plurality of types of data of tissue used to form a pathological section specimen; a storage part configured to store the data of the tissue; a parameter generation part configured to generate parameters based on the data of the tissue acquired by the acquisition part, the parameters being used when preparing the pathological section specimen; and a pathological section specimen preparation part configured to prepare the pathological section specimen by using the parameters generated by the parameter generation part.

In the automatic thin-cutting device according to the aspect of the present invention, the acquisition part may acquire the data of the tissue from a host system.

In the automatic thin-cutting device according to the aspect of the present invention, the acquisition part may acquire the data of the tissue by measuring a paraffin block in which the tissue is embedded.

In the automatic thin-cutting device according to the aspect of the present invention, the acquisition part may acquire the data of the tissue by receiving an input of data from a user.

A parameter generation device according to another aspect of the present invention includes: an acquisition part configured to acquire a plurality of types of data of tissue used to form a pathological section specimen; a storage part configured to store the data of the tissue; and a parameter generation part configured to generate parameters based on the data of the tissue acquired by the acquisition part, the parameters being used when preparing the pathological section specimen.

An automatic thin-cutting method according to still another aspect of the present invention includes: an acquisition step of acquiring a plurality of types of data of tissue used to form a pathological section specimen; a parameter generation step of generating parameters based on the data of the tissue acquired in the acquisition step, the parameters being used when preparing the pathological section specimen; and a pathological section specimen preparation step of preparing the pathological section specimen using the parameters generated in the parameter generation step.

A program according to still another aspect of the present invention causes a computer to execute: an acquisition step of acquiring a plurality of types of data of tissue used to form a pathological section specimen; a parameter generation step of generating parameters based on the data of the tissue acquired in the acquisition step, the parameters being used when preparing the pathological section specimen; and a pathological section specimen preparation step of preparing the pathological section specimen using the parameters generated in the parameter generation step.

Advantage of Invention

According to the aspects of the present invention, the acquisition part acquires a plurality of types of data of tissue used to form a pathological section specimen. The storage part stores the data of the tissue. The parameter generation part generates parameters, which are used when preparing the pathological section specimen, based on the data of the tissue acquired by the acquisition part. A pathological section specimen preparation part prepares the pathological section specimen using the parameters generated by the parameter generation part. Therefore, the parameters used when preparing a pathological section specimen can be automatically generated more flexibly.

DESCRIPTION OF EMBODIMENTS

Figures 1, 2:
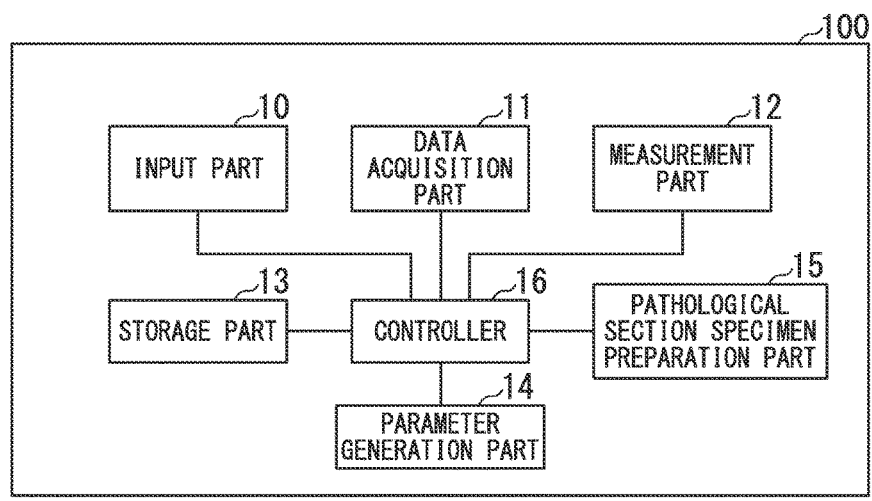
FIG. 1 is a block diagram showing the configuration of an automatic thin-cutting device in an embodiment of the present invention.
FIG. 2 is a schematic diagram showing the data structure of a reference table in the present embodiment.

Hereinafter, an embodiment of the present invention will be described with reference to the diagrams. FIG. 1 is a block diagram showing the configuration of an automatic thin-cutting device in the present embodiment. In the shown example, an automatic thin-cutting device 100 includes an input part 10, a data acquisition part 11, a measurement part 12, a storage part 13, a parameter generation part 14, a pathological section specimen preparation part 15, and a controller 16. In the present embodiment, any or all of the input part 10, the data acquisition part 11, and the measurement part 12 operate as an acquisition part. As will be described in detail later, the acquisition part can acquire a plurality of types of data of tissue used to form a pathological section specimen.

The input part 10 receives an input of data from the user. The data acquisition part 11 acquires data from the host system (pathological support system). The measurement part 12 measures a paraffin block in which tissue is embedded. The storage part 13 stores data that is used when each unit of the automatic thin-cutting device 100 operates. For example, the storage part 13 stores a device internal database (hereinafter, simply referred to as a database).

In addition, the storage part 13 stores a reference table in advance. The database and the reference table will be described later.

The parameter generation part 14 generates parameters used when preparing a pathological section specimen based on all or part of the data received by the input part 10, the data acquired by the data acquisition part 11, the measurement result of the measurement part 12, and the reference table stored in the storage part 13.

The pathological section specimen preparation part 15 cuts a thin section from the paraffin block in which tissue is embedded based on the parameters generated by the parameter generation part 14 and pastes the thin section on the slide glass, thereby preparing a pathological section specimen. The controller 16 controls each part provided in the automatic thin-cutting device 100.

A device including the input part 10, the data acquisition part 11, the measurement part 12, the storage part 13, and the parameter generation part 14 that have been described above is assumed to be a parameter generation device.

Next, data that the data acquisition part 11 acquires from the host system will be described. The host system is, for example, an online system (pathological support system) of a hospital, and is connected to the automatic thin-cutting device 100 through a network that enables communication with the automatic thin-cutting device 100. For example, the host system stores "block ID", "print information", "organ type", "dyeing method", "defatting state", "decalcification state", and "slide number" so as to be associated with each "block ID". The data acquisition part 11 acquires these pieces of data, and stores them in the database that is stored in the storage part 13.

When the host system stores the above-described data in a shared folder, the data acquisition part 11 may acquire the above-described data asynchronously from the shared folder instead of acquiring the data directly from the host system.

The "block ID" is an ID for uniquely identifying a paraffin block in which tissue used to form a pathological section specimen is embedded. The "print information" is information to be printed on the slide glass of the pathological section specimen. The "organ type" is information indicating the type of tissue used to form a pathological section specimen. The "dyeing method" is information indicating a dyeing method of tissue used to form a pathological section specimen. The "defatting state" is information indicating the defatting state of tissue used to form a pathological section specimen. The "decalcification state" is information indicating the decalcification state of tissue used to form a pathological section specimen. The "slide number" is information indicating the number of pathological section specimens.

Next, data measured by the measurement part 12 will be described. The measurement part 12 measures the height ("block height"), inclination ("block inclination"), and size ("block size") of the paraffin block in which tissue is embedded, for example. The measurement part 12 stores the measurement result in the database that is stored in the storage part 13.

Next, the database stored in the storage part 13 will be described. As described above, data that the data acquisition part 11 acquires from the host system and data that the measurement part 12 measures are stored in the database. Specifically, "print information", "organ type", "dyeing method", "defatting state", "decalcification state", "slide number", "block height", "block inclination", and "block size" for each "block ID" are stored in the database.

In addition, when data that cannot be acquired from the host system or data that cannot be measured by the measurement part 12 is present in the data described above, the user may input the data directly into the input part 10. In this case, the input part 10 stores the input data in the database stored in the storage part 13. The above data stored in a database is assumed to be data of tissue to be pasted to the pathological section specimen to be prepared.

Next, a reference table stored in advance in the storage part 13 will be described. FIG. 2 is a schematic diagram showing the data structure of a reference table stored in advance in the storage part 13 in the present embodiment. The reference table has data items of "organ type", "dyeing method", "defatting state", "decalcification state", "rough cutting recipe", "main cutting recipe", "spreading recipe", "used slide glass", and "used dyeing case", and data of each data items is stored so as to be associated with each other in same row.

In the data item "organ type", information indicating the type of tissue used to form a pathological section specimen is stored. In the data item "dyeing method", information indicating a dyeing method to dye a tissue used to form a pathological section specimen is stored. In the data item "defatting state", information indicating the defatting state of tissue used to form a pathological section specimen is stored. In the data item "decalcification state", information indicating the decalcification state of tissue used to form a pathological section specimen is stored.

In the data item "rough cutting recipe", information indicating a method of rough cutting, which is performed when cutting a pathological section from a paraffin block in which tissue used to form a pathological section specimen is embedded, is stored. The "rough cutting recipe" includes a plurality of rough cutting steps, and each step includes a cutting speed, a cutting thickness, and the number of cuts.

In the data item "main cutting recipe", information indicating a method of main cutting, which is performed when cutting a pathological section from a paraffin block in which tissue used to form a pathological section specimen is embedded, is stored. The "main cutting recipe" includes a cutting thickness, a cutting speed, and humidification time, the number of sections, the strength of Unroll-Air, the length of time of Unroll-Air, and blow timing of Unroll-Air or a position of Unroll-Air. The Unroll-Air opens a section curled at the time of thin-cutting, for example.

In the data item "spreading recipe", information indicating a method of spreading a pathological section after main cutting is stored. In the data item "used slide glass", information indicating the slide glass on which a pathological section is pasted is stored. In the data item "used dyeing case", information indicating a case in which a pathological section specimen is housed is stored.

In the present embodiment, if "organ type", "dyeing method", "defatting state", and "decalcification state" are uniquely determined, "rough cutting recipe", "main cutting recipe", "spreading recipe", "used slide glass", and "used dyeing case" that are parameters used when preparing a pathological section specimen are uniquely determined. That is, in the reference table, parameters used when preparing a pathological section specimen are defined with respect to the combination of data stored in the database by the host system, the input part 10, or the measurement part 12.

In the example shown in FIG. 2, the value stored in the data item "organ type" in row 201 is "T1", the value stored in the data item "dyeing method" is "S1", the value stored in the data item "defatting state" is "Y", and the value stored in the data item "decalcification state" is "N". In addition, the value stored in the data item "rough cutting recipe" in the row 201 is "F1", the value stored in the data item "main cutting recipe" is "Set", the value stored in the data item "spreading recipe" is "F1", the value stored in the data item "used slide glass" is "1", and the value stored in the data item "used dyeing case" is "1".

This indicates that, when data in which "organ type" is "T1", "dyeing method" is "S1", "defatting state" is "Y", and "decalcification state" is "N" is acquired from the database, the parameter generation part 14 sets "rough cutting recipe", "main cutting recipe", "spreading recipe", "used slide glass", and "used dyeing case", which are parameters used when preparing a pathological section specimen, to "F1", "Sc1", "F1", "1", and "1", respectively. Values stored in the data items for the other rows are shown in FIG. 2.

Therefore, the parameter generation part 14 can generate parameters used when preparing a pathological section specimen based on the data stored in the database stored in the storage part 13 and the data stored in the reference table stored in the storage part 13. Parameters used when preparing a pathological section specimen, which are generated by the parameter generation part 14, are "print information", "block height", "block inclination", "block size", "rough cutting recipe", "main cutting recipe", "spreading recipe", "used slide glass", "used dyeing case", "collection number", and "collection timing", for example. The "collection number" is determined from the "slide number", and the "collection timing" is determined by the "block size".

Figure 3:
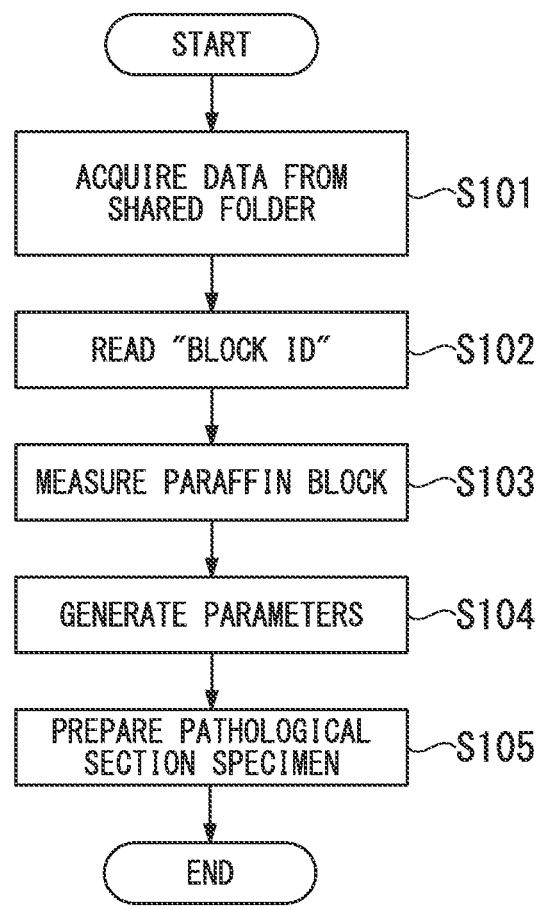
FIG. 3 is a flowchart showing the operation procedure of the automatic thin-cutting device in the present embodiment.

Next, the operation procedures of the automatic thin-cutting device 100 will be described. FIG. 3 is a flowchart showing the operation procedures of the automatic thin-cutting device 100 in the present embodiment. The host system stores "block ID", "print information", "organ type", "dyeing method", "defatting state", "decalcification state", and "slide number" in a shared folder when necessary. As described above, "print information", "organ type", "dyeing method", "defatting state", "decalcification state", and "slide number" are associated with "block ID".

(Step S101)
The data acquisition part 11 acquires "block ID", "print information", "organ type", "dyeing method", "defatting state", "decalcification state", and "slide number" from the shared folder, and stores these in a database stored in the storage part 13. Then, the process proceeds to step S102.

(Step S102)
The pathological section specimen preparation part 15 reads the "block ID" of a paraffin block set in the automatic thin-cutting device 100. Then, the process proceeds to step S103.

(Step S103)
The pathological section specimen preparation part 15 sets the paraffin block, of which the "block ID" has been read in the process of step S102, on the cutting table. Then, the measurement part 12 measures the height, inclination, and block size of the paraffin block set on the cutting table, and stores the measurement result in the database stored in the storage part 13. Then, the process proceeds to step S104.

(Step S104)
The parameter generation part 14 reads data, which is associated with the "block ID" that has been read by the pathological section specimen preparation part 15 in the process of step S102, from the database and the reference table stored in the storage part 13, thereby generating parameters used when preparing a pathological section specimen. Then, the process proceeds to step S105. The method used when the parameter generation part 14 generates parameters used when preparing a pathological section specimen is the same as described above.

(Step S105)
The pathological section specimen preparation part 15 prepares a pathological section specimen using the parameters used when preparing a pathological section specimen, which have been generated by the parameter generation part 14 in the process of step S104. Then, the process is ended.

In the procedure shown in FIG. 3, the data acquisition part 11 acquires the data stored in the database from the shared folder. However, the user may input the data directly into the input part 10, without being limited to the above. In addition, although the measurement part 12 measures the height, inclination, and size of the paraffin block in the procedure shown in FIG. 3, the present invention is not limited thereto. For example, the user may input the measurement result directly into the input part 10. Alternatively, when the measurement result is already stored in the host system, the measurement result may be acquired by the data acquisition part 11 similar to other data. In addition, any or all of the data acquisition part 11, the measurement part 12, and the input part 10 may be used. Therefore, for example, even in the case of additionally preparing a pathological section specimen suddenly, the user can input the data directly into the input part 10 to prepare the pathological section specimen.

In the procedure shown in FIG. 3, in the process of step S101, the pathological section specimen preparation part 15 reads the "block ID" of the paraffin block set in the automatic thin-cutting device 100. However, the present invention is not limited thereto. For example, the user may input the "block ID" directly into the input part 10.

In addition, in the example described above, the parameter generation part 14 generates the parameters which are used when preparing a pathological section specimen by using the reference table. However, the present invention is not limited thereto. For example, as described above, the parameters used when preparing a pathological section specimen may be generated using a reference table having a simple arrangement. For example, the parameters used when preparing a pathological section specimen may be generated by scoring the data stored in the database and performing a numerical calculation.

According to the present embodiment, the storage part 13 stores the reference table as described above. In the reference table, parameters used when preparing a pathological section specimen are defined with respect to the combination of data stored in the database by the host system, the input part 10, or the measurement part 12. In addition, the input part 10, the data acquisition part 11, or the measurement part 12 acquires the data of a paraffin block in which tissue used to form a pathological section specimen to be prepared is embedded or the data of the tissue used to form a pathological section specimen to be prepared, and stores the data in the database. The parameter generation part 14 generates the parameters used when preparing a pathological section specimen based on the data stored in the database and the reference table. Therefore, the parameters used when preparing a pathological section specimen can be automatically generated more flexibly.

While an embodiment of the invention has been described in detail with reference to the diagrams, the specific configuration is not limited to the embodiment, and design and the like are also included without departing from the scope of the invention.

In addition, all or some of the functions of the respective parts provided in the automatic thin-cutting device 100 described above may be realized by recording a program for realizing the functions in a computer-readable recording medium, reading the program recorded in the recording medium into a computer system, and executing the program. The "computer system" referred to herein is intended to include an OS or hardware, such as a peripheral device.

Examples of the "computer-readable recording medium" include portable media, such as a flexible disk, a magneto-optic disc, a ROM, and a CD-ROM, and a storage device, such as a hard disk built into a computer system. In addition, examples of the "computer-readable recording medium" may also include a recording medium that stores a program dynamically for a short period of time like a network, such as the Internet, or a communication line when transmitting a program through a communication line, such as a telephone line, and include a recording medium that stores a program for a predetermined period of time like a volatile memory in a computer system that serves as a server or a client in that case. The above program may be a program for realizing some of the functions described above or may be a program capable of realizing the above functions in combination with a program already recorded in the computer system.

REFERENCE SIGNS LIST

10: input part
11: data acquisition part
12: measurement part
13: storage part
14: parameter generation part
15: pathological section specimen preparation part
16: controller
100: automatic thin-cutting device

What is claimed is:

1. An automatic thin-cutting method, comprising:
a data acquisition step of acquiring a tissue data of tissue used to form a pathological section specimen, the tissue data including information indicating a type of the tissue, a dyeing method used to dye the tissue, a defatting state of the tissue, a decalcification state of the tissue, and a slide number information indicating a number of pathological section specimens;
a measurement step of measuring a block height, a block inclination and a block size of a paraffin block in which the tissue is embedded,
a parameter generation step of generating parameters based on the data acquired by the data acquisition step and the data measured by the measurement step and a reference table that stores a predetermined plurality of sets of data items respectively including different combinations of a type of the tissue, a dyeing method of a tissue, a defatting state of a tissue, a decalcification state of a tissue, a rough cutting recipe indicating a method of rough cutting which is performed when cutting a pathological section from a paraffin block, a main cutting recipe indicating a method of main cutting which is performed when cutting a pathological section from a paraffin block, a spreading recipe indicating a method of spreading a pathological section after the main cutting, a used slide glass information indicating a slide glass on which a pathological section is pasted, and a used dyeing case information indicating a case in which a pathological section specimen is housed, wherein the parameters indicate a preparation method of the pathological section specimen prepared by cutting out a tissue from the paraffin block based on the data of the block height, the block inclination, the block size, the rough cutting recipe, the main cutting recipe, the spreading recipe, the used slide glass information, the used dyeing case information, a collection number which is determined from the slide number information and a collection timing which is determined by block size;
a pathological section specimen preparation step of automatically preparing the pathological section specimen using the parameters generated in the parameter generation step; and
cutting the tissue using an automatic thin-cutting device.

2. The automatic thin-cutting method according to claim 1, wherein the rough cutting recipe includes one or a plurality of rough cutting steps, and each step includes at least one of a cutting speed, a cutting thickness, and a number of cuts.

3. The automatic thin-cutting method according to claim 1, wherein the main cutting recipe includes at least one of a cutting thickness, a cutting speed, and humidification time, a number of sections, a strength of Unroll-Air that opens a section curled at the time of thin-cutting, a length of time of Unroll-Air, and blow timing of Unroll-Air or a position of Unroll-Air.

4. One or more non-transitory computer readable memories which store, in combination or singularly, instructions that, when executed by one or more computers, cause the following operations: to execute:
 a data acquisition operation comprising step of acquiring a tissue data of tissue used to form a pathological section specimen, the tissue data including information indicating a type of the tissue, a dyeing method used to dye the tissue, a defatting state of the tissue and a decalcification state of the tissue, and a slide number information indicating a number of pathological section specimens;
 a measurement operation comprising step of measuring a block height, a block inclination and a block size of a paraffin block in which the tissue is embedded,
 a parameter generation step of generating parameters based on the data acquired by the data acquisition step and the data measured by the measurement step and a reference table that stores a predetermined plurality of sets of data items respectively including different combinations of a type of the tissue, a dyeing method of a tissue, a defatting state of a tissue, a decalcification state of a tissue, a rough cutting recipe indicating a method of rough cutting which is performed when cutting a pathological section from a paraffin block, a main cutting recipe indicating a method of main cutting which is performed when cutting a pathological section from a paraffin block, a spreading recipe indicating a method of spreading a pathological section after the main cutting, a used slide glass information indicating a slide glass on which a pathological section is pasted, and a used dyeing case information indicating a case in which a pathological section specimen is housed, wherein the parameters indicate a preparation method of the pathological section specimen prepared by cutting out a tissue from the paraffin block based on the data of the block height, the block inclination, the block size, the rough cutting recipe, the main cutting recipe, the spreading recipe, the used slide glass information, the used dyeing case information, a collection number which is determined from the slide number information and a collection timing which is determined by block size;
 a pathological section specimen preparation operation comprising automatically preparing the pathological section specimen using the parameters generated in the parameter generation operation; and
 causing an automatic thin-cutting device to cut the tissue.

5. The one or more non-transitory computer readable memories according to claim 4, wherein the rough cutting recipe includes one or a plurality of rough cutting steps, and each step includes at least one of a cutting speed, a cutting thickness, and a number of cuts.

6. The one or more non-transitory computer readable memories according to claim 4, wherein the main cutting recipe includes at least one of a cutting thickness, a cutting speed, and humidification time, a number of sections, a strength of Unroll-Air that opens a section curled at the time of thin-cutting, a length of time of Unroll-Air, and blow timing of Unroll-Air or a position of Unroll-Air.

* * * * *